(12) United States Patent
Chen et al.

(10) Patent No.: US 9,944,983 B2
(45) Date of Patent: Apr. 17, 2018

(54) METHOD OF SCREENING A PLURALITY OF SINGLE SECRETING CELLS FOR FUNCTIONAL ACTIVITY

(71) Applicant: Single Cell Technology, Inc., San Jose, CA (US)

(72) Inventors: Chun-Nan Chen, San Jose, CA (US); James O. Bowlby, Jr., San Jose, CA (US)

(73) Assignee: Single Cell Technology, Inc., San Jose, CA (US)

( * ) Notice: Subject to any disclaimer, the term of this patent is extended or adjusted under 35 U.S.C. 154(b) by 140 days.

(21) Appl. No.: 14/364,520

(22) PCT Filed: Dec. 12, 2012

(86) PCT No.: PCT/US2012/069205
§ 371 (c)(1),
(2) Date: Jun. 11, 2014

(87) PCT Pub. No.: WO2013/090404
PCT Pub. Date: Jun. 20, 2013

(65) Prior Publication Data
US 2015/0051098 A1 Feb. 19, 2015

Related U.S. Application Data

(60) Provisional application No. 61/630,493, filed on Dec. 13, 2011.

(51) Int. Cl.
*C12N 15/10* (2006.01)
*C12Q 1/68* (2018.01)
(Continued)

(52) U.S. Cl.
CPC ....... *C12Q 1/6874* (2013.01); *C12N 15/1034* (2013.01); *C12N 15/1086* (2013.01); *C40B 30/04* (2013.01); *C40B 30/06* (2013.01)

(58) Field of Classification Search
None
See application file for complete search history.

(56) References Cited

U.S. PATENT DOCUMENTS

| 2010/0034807 A1* | 2/2010 | Moyle | C07K 16/00 424/130.1 |
|---|---|---|---|
| 2010/0035763 A1* | 2/2010 | Chen | C07K 16/2896 506/9 |

(Continued)

FOREIGN PATENT DOCUMENTS

WO WO2010085275 A1 7/2010

OTHER PUBLICATIONS

454 Life Sciences (2007) "How is genome sequencing done?", obtained from http://www.454.com/downloads/news-events/how-genome-sequencing-is-done_FINAL.pdf.*

(Continued)

*Primary Examiner* — Karen S. Weiler
(74) *Attorney, Agent, or Firm* — Convergent Law Group LLP

(57) ABSTRACT

This invention generally relates to methods, devices and kits for screening a plurality of single secreting cells for functional activity of the secreted molecules by measuring the amount of reporter gene mRNA produced in one or more reporter cells in response to the secreted molecules.

7 Claims, 5 Drawing Sheets

Detection of a Receptor Agonist

(51) Int. Cl.
C40B 30/04 (2006.01)
C40B 30/06 (2006.01)

(56) References Cited

U.S. PATENT DOCUMENTS

2010/0255471 A1 10/2010 Clarke et al.
2011/0160078 A1* 6/2011 Fodor .................. C12Q 1/6809
506/9
2011/0190148 A1 8/2011 Chen et al.
2013/0252258 A1* 9/2013 Bocchi ............. G01N 33/56972
435/7.21

OTHER PUBLICATIONS

PCT International Search Report and Written Opinion of the International Searching Authority, dated Mar. 27, 2013, Application No. PCT/US12/69205.

* cited by examiner

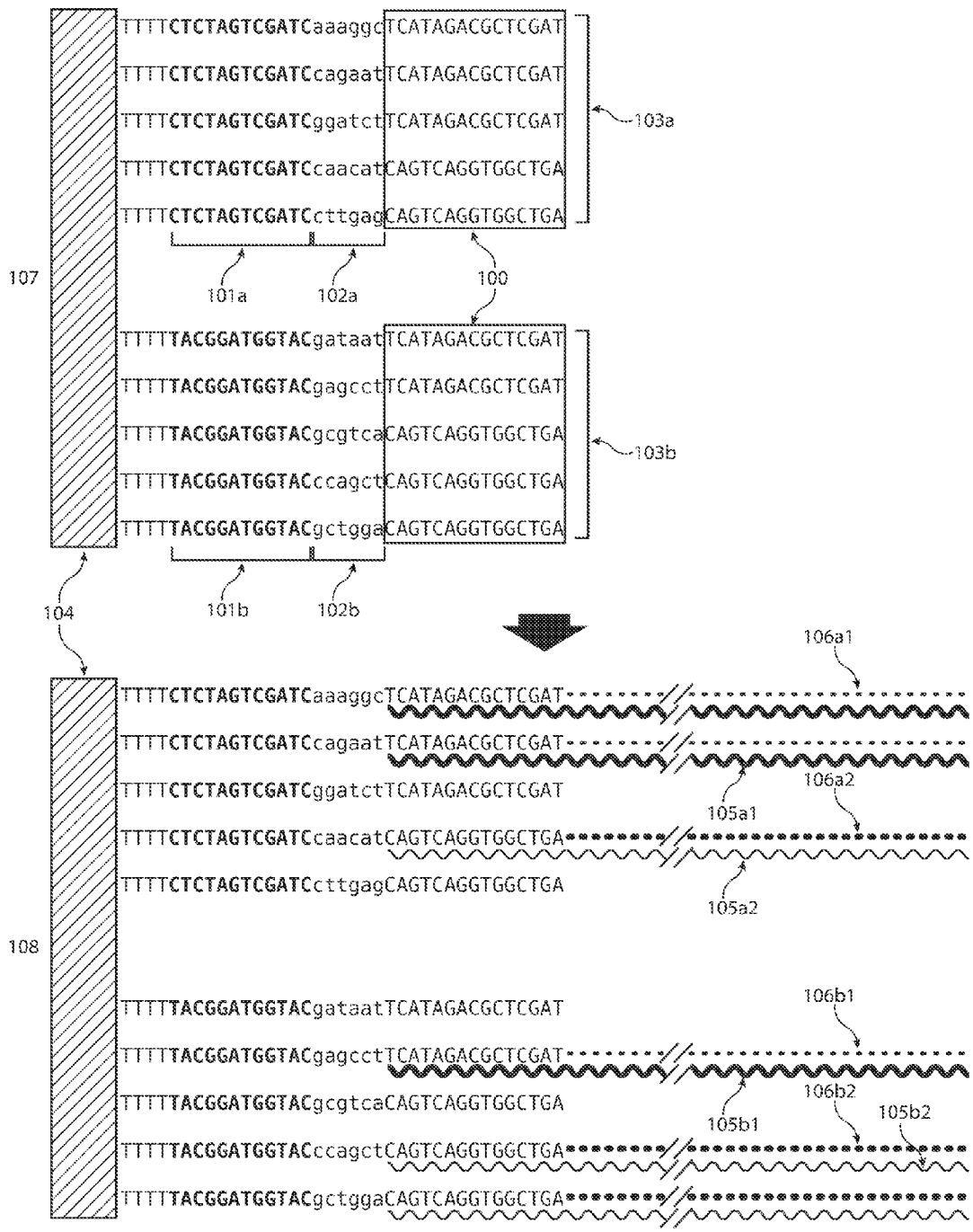
FIG. 1. Anatomy of two adjacent features with their mRNA capture probes on a DNA microarray

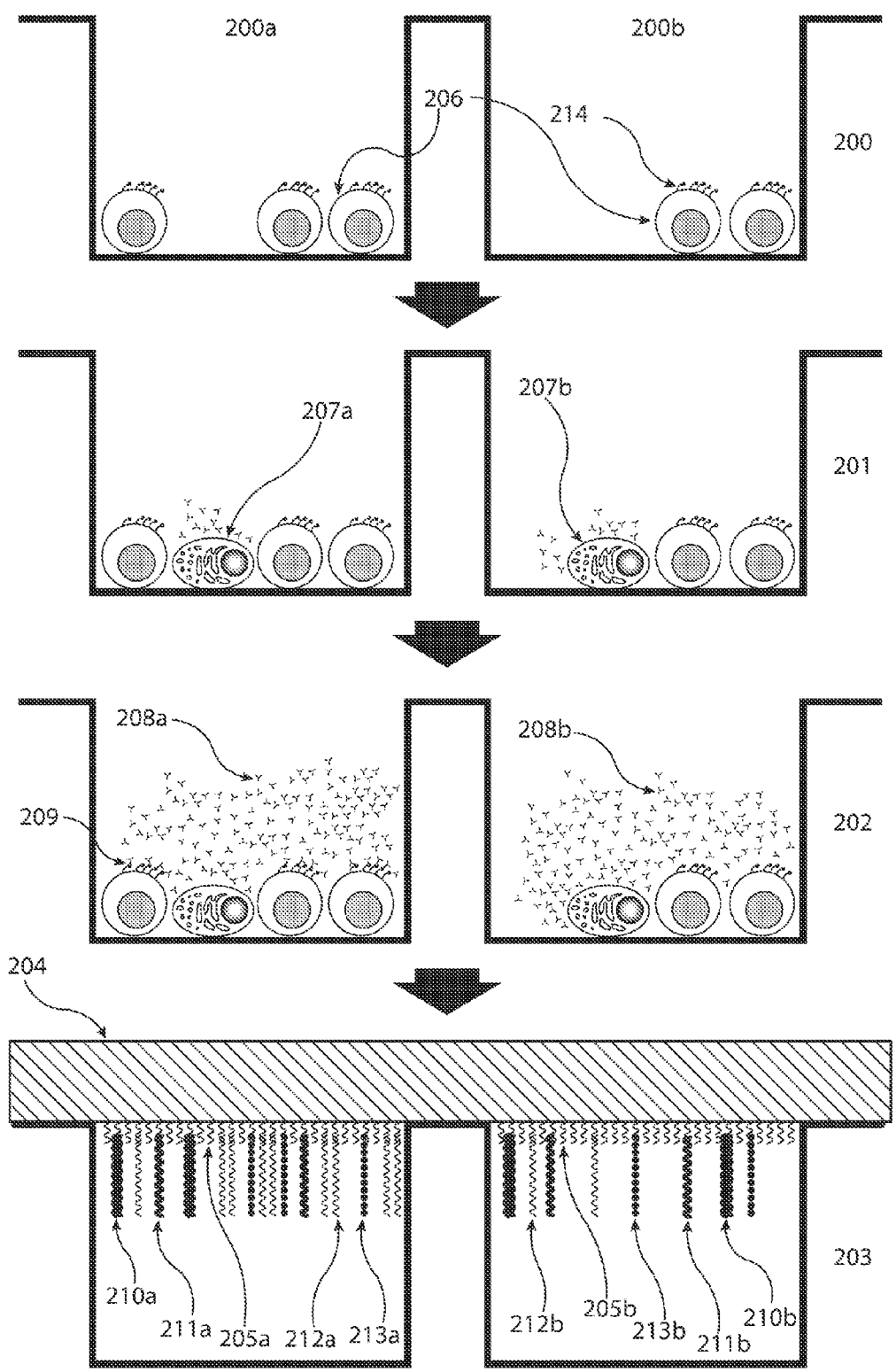
FIG. 2. Detection of a Receptor Agonist

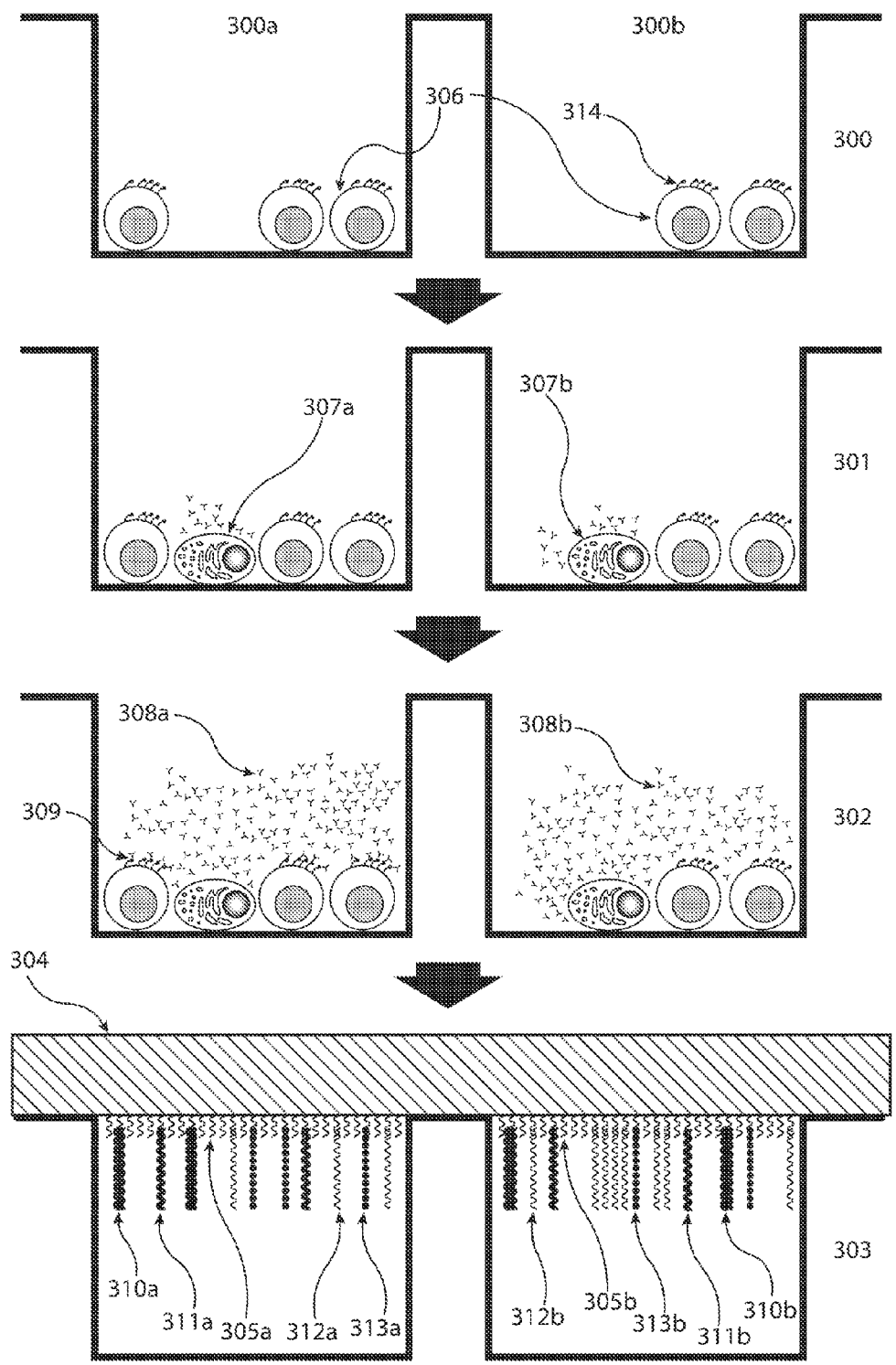
FIG. 3. Detection of a inverse agonist, a type of Receptor Agonist

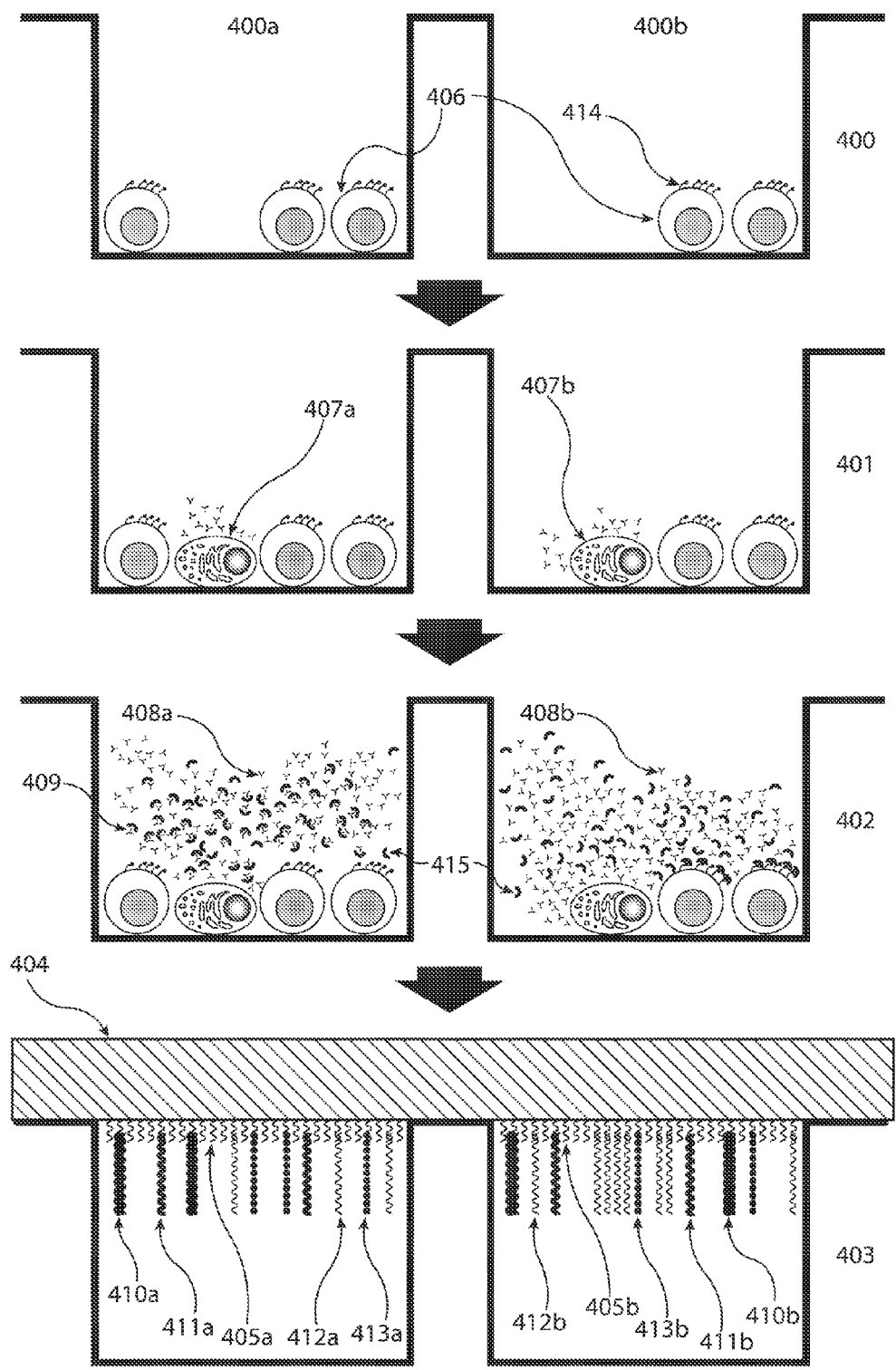
FIG. 4. Detection of a Modulator

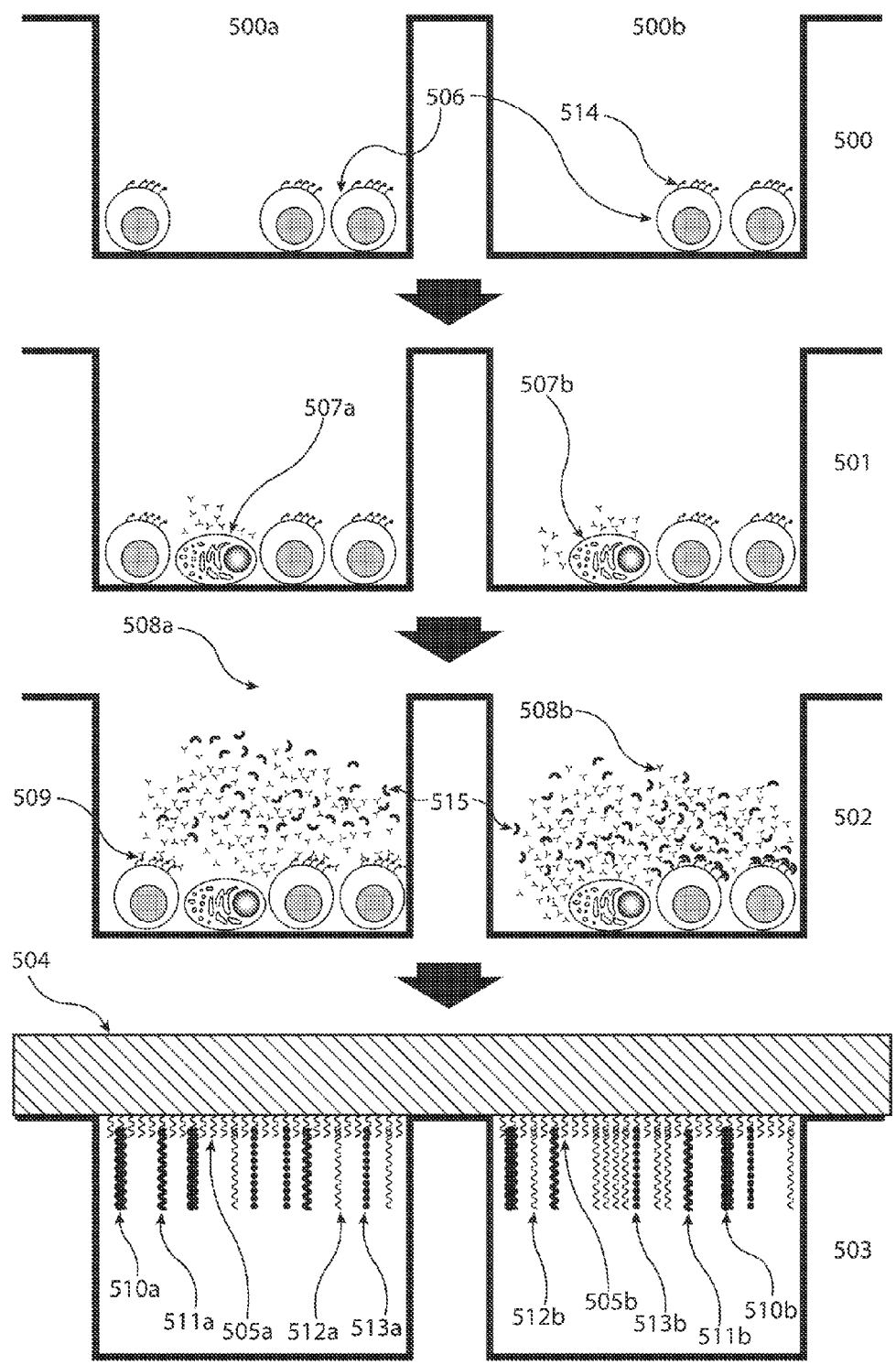
FIG. 5. Detection of a Receptor Antagonist

SEQUENCE LISTING

```
<160> NUMBER OF SEQ ID NOS: 10

<210> SEQ ID NO 1
<211> LENGTH: 37
<212> TYPE: DNA
<213> ORGANISM: Artificial Sequence
<220> FEATURE:
<223> OTHER INFORMATION: Demonstrative oligonucleotide sequence

<400> SEQUENCE: 1
ttttctctag tcgatcaaag gctcatagac gctcgat                              37

<210> SEQ ID NO 2
<211> LENGTH: 37
<212> TYPE: DNA
<213> ORGANISM: Artificial Sequence
<220> FEATURE:
<223> OTHER INFORMATION: Demonstrative oligonucleotide sequence

<400> SEQUENCE: 2
ttttctctag tcgatccaga attcatagac gctcgat                              37

<210> SEQ ID NO 3
<211> LENGTH: 37
<212> TYPE: DNA
<213> ORGANISM: Artificial Sequence
<220> FEATURE:
<223> OTHER INFORMATION: Demonstrative oligonucleotide sequence

<400> SEQUENCE: 3
ttttctctag tcgatcggat cttcatagac gctcgat                              37

<210> SEQ ID NO 4
<211> LENGTH: 37
<212> TYPE: DNA
<213> ORGANISM: Artificial Sequence
<220> FEATURE:
<223> OTHER INFORMATION: Demonstrative oligonucleotide sequence

<400> SEQUENCE: 4
ttttctctag tcgatccaac atcagtcagg tggctga                              37

<210> SEQ ID NO 5
<211> LENGTH: 37
<212> TYPE: DNA
<213> ORGANISM: Artificial Sequence
```

```
<220> FEATURE:
<223> OTHER INFORMATION: Demonstrative oligonucleotide sequence

<400> SEQUENCE: 5
ttttctctag tcgatccttg agcagtcagg tggctga                                  37

<210> SEQ ID NO 6
<211> LENGTH: 37
<212> TYPE: DNA
<213> ORGANISM: Artificial Sequence
<220> FEATURE:
<223> OTHER INFORMATION: Demonstrative oligonucleotide sequence

<400> SEQUENCE: 6
tttttacgga tggtacgata attcatagac gctcgat                                  37

<210> SEQ ID NO 7
<211> LENGTH: 37
<212> TYPE: DNA
<213> ORGANISM: Artificial Sequence
<220> FEATURE:
<223> OTHER INFORMATION: Demonstrative oligonucleotide sequence

<400> SEQUENCE: 7
tttttacgga tggtacgagc cttcatagac gctcgat                                  37

<210> SEQ ID NO 8
<211> LENGTH: 37
<212> TYPE: DNA
<213> ORGANISM: Artificial Sequence
<220> FEATURE:
<223> OTHER INFORMATION: Demonstrative oligonucleotide sequence

<400> SEQUENCE: 8
tttttacgga tggtacgcgt cacagtcagg tggctga                                  37

<210> SEQ ID NO 9
<211> LENGTH: 37
<212> TYPE: DNA
<213> ORGANISM: Artificial Sequence
<220> FEATURE:
<223> OTHER INFORMATION: Demonstrative oligonucleotide sequence

<400> SEQUENCE: 9
tttttacgga tggtacccag ctcagtcagg tggctga                                  37

<210> SEQ ID NO 10
<211> LENGTH: 37
<212> TYPE: DNA
<213> ORGANISM: Artificial Sequence
<220> FEATURE:
<223> OTHER INFORMATION: Demonstrative oligonucleotide sequence

<400> SEQUENCE: 10
tttttacgga tggtacgctg gacagtcagg tggctga                                  37
```

METHOD OF SCREENING A PLURALITY OF SINGLE SECRETING CELLS FOR FUNCTIONAL ACTIVITY

STATEMENT OF RELATED CASES

The present application claims priority to U.S. provisional application 61/630,493 filed Dec. 13, 2011.

FIELD OF THE INVENTION

This invention generally relates to methods, devices and kits for screening a plurality of single secreting cells for functional activity of secreted molecules.

BACKGROUND

Cells that secrete molecules are an important source of therapeutically important biological molecules, and thus it is often valuable to screen secreted molecules from a population of secreting cells for certain functional properties. Useful secreting cells may be, for example, murine or human plasma cells or other antibody secreting cells, where the secreted antibody may block the binding of a cytokine to its cognate receptor thereby disrupting a signal transduction event that may underlie the physiopathology of a disease. Therefore, such blocking antibodies possess tremendous therapeutic value and hence are of interest to the pharmaceutical industry. Alternatively, engineered bioactive molecules such as a cytokine with a variant amino acid at a strategic residue can be screened for enhanced binding to a cognate receptor. Currently, such functional screening is a laborious procedure typically done with a large number of cells in 96-well plates.

Much work has been done to engineer cells to "report" when a ligand binds to a receptor expressed on the surface of the cells. Engineering has been desirable because the cells may not have readily assayable changes in response to such a binding event. Therefore, certain genes are chosen as reporters because the characteristics they confer when expressed are easily identified and measured. Some reporter cells are comprised of reporter genes encoding readily assayable proteins under the control of well-characterized transcriptional regulatory elements responding as part of a well-known signal transduction pathway. Examples of common reporter genes are LacZ (encoding beta-galactosidase), luc (encoding firefly luciferase), luxCDABE (encoding bacterial luciferase) and GFP (encoding jellyfish green fluorescent protein) (Ghim et al., BMB reports, 2010, 451:460). One of the most commonly used signal transduction pathways is the NF-κB activation pathway. Reporter genes are typically placed under the control of NF-κB regulatory elements and are used to screen molecules interacting with the relevant receptor, which causes activation of NF-κB and is manifested by expression of the reporter genes.

There are many limitations to each of the aforementioned reporter genes. The lacZ assay requires expensive and potentially toxic chemicals, the luc assay requires expensive luciferin, bacterial luciferase cannot be used in eukaryotic cells, and GFP is so stable it cannot be used to report short term negative processes where the GFP signal needs to diminish quickly (Ghim et al., supra). Since the above-stated reporter systems typically are used on a large population of cells, it is difficult to employ them in nanofabricated constructs on a limited number of cells. Furthermore, these reporter assays require translation of the protein products to visualize the output, which often takes hours or even up to a day.

In addition to the above-mentioned reporter systems utilizing expressed proteins, microarrays have been used to investigate multi-gene mRNA expression between multiple populations of tissues or cells. Microarrays allow many mRNA sequences to be sampled at the same time, but because of the expense of preparation and handling the number of tissue samples is generally small (less than 20) and the cell population large (more than a million cells). Therefore, the use of mRNA expression as a reporter system is a serial and labor intensive process.

In order to correct the deficiencies of the current state of the art, a method is needed where a single cell secreting a biologically active moiety may be tested by one or more reporter cells and/or one or more types of reporter cells, and where an artificial reporter gene(s) does not need to be engineered into the reporter cell(s) to read out the response upon a binding event between a receptor and the active moiety, or upon disruption of binding. The present invention generally relates to methods, devices and kits directed to these and similar utilities, such methods, devices and kits being further described herein.

SUMMARY OF THE INVENTION

This invention generally relates to methods, devices and kits for screening a plurality of single secreting cells for functional activity of molecules secreted by them by measuring the Normalized Copy Number (NCN) of mRNA from one or more reporter genes produced by one or more types of reporter cells in response to the secreted molecules acting as a receptor agonist, as a receptor antagonist, or as a modulator. In one embodiment, a plurality of secreting cells are spread and settled into a plurality of microwells with a majority of microwells containing a single secreting cell. One or more types of reporter cells are also placed in the microwells. Molecules secreted by the secreting cells are captured on one or more support surfaces brought into contact with the microwells, and at the same time the secreted molecules are allowed to interact with the reporter cells in the microwells. The secreted molecules may act as a receptor agonist or receptor antagonist, and subsequently the secreting cells and reporter cells are lysed releasing mRNA encoding the secreted molecules, the mRNA from one or more reporter genes in one or more types of reporter cells, and housekeeping gene(s) from the reporter cells. The mRNAs are captured on an oligonucleotide capture support containing mRNA capture oligos comprising unique nucleotide tags and, optionally, a random code at each location on the oligonucleotide capture support corresponding to each microwell location. The captured mRNA on the oligonucleotide capture support is converted into cDNA incorporating the tags and optionally the random code, and the tagged and coded cDNA is sequenced using NGS technology. In addition, the binding kinetic properties of the secreted molecules to one or more specific moieties are measured.

The mRNA sequence encoding the secreted molecules is then associated with the measured binding kinetic properties and the Absolute Copy Number (ACN) of the mRNA from one or more reporter genes of the reporter cells is determined. Furthermore, the ACN of the mRNA of housekeeping gene(s) of the reporter cells is determined and used to calculate the NCN of mRNA of one or more reporter genes of the reporter cells. If more than one type of reporter cells is used, typically the ACN of one or more housekeeping genes is determined for each type of reporter cell. The NCN of the mRNA of one or more reporter genes of the reporter cells associated with a given secreted molecule in a microwell can be used to assess the secreted molecule's functional activity when compared to the NCN of the mRNA of one or more reporter genes of the reporter cells associated with other secreted molecules in a microwell or the NCN of the mRNA of one or more reporter genes of the reporter cells associated with an empty microwell.

In another embodiment, a plurality of secreting cells are spread and settled into a plurality of microwells with a majority of microwells containing a single secreting cell. One or more types of reporter cells are also placed in the microwells. Molecules secreted by the secreting cells are captured on one or more support surfaces brought into contact with the microwells, at the same time the secreted molecules are allowed to interact with the reporter cells in the microwells as a modulator in the presence of a naturally-occurring receptor agonist or receptor antagonist. Subsequently the secreting cells and reporter cells are lysed releasing their mRNA. The mRNA encoding the secreted molecules, the mRNA from one or more reporter genes in one or more types of reporter cells, and housekeeping gene(s) from each type of the reporter cells are captured on an oligonucleotide capture support containing mRNA capture oligos comprising unique nucleotide tags and random code at each location on the oligonucleotide capture support corresponding to each microwell location. The captured mRNA on the oligonucleotide capture support is converted into cDNA incorporating the tags and optionally random code, and tagged and coded cDNA is sequenced using NGS technology. In addition, the kinetic properties of the secreted molecules to one or more specific moieties are measured. The mRNA sequence encoding the secreted molecules is associated with the measured kinetic properties and Absolute Copy Number (ACN) of the mRNA of one or more reporter genes from each type of reporter cells is determined. The ACN of the mRNA of housekeeping gene(s) of each type of reporter cells is determined and is used to calculate the NCN of mRNA of one or more reporter genes from each type of reporter cells. The NCN of the mRNA of one or more reporter genes of the reporter cells associated with a given secreted molecule in a microwell can be used to assess the secreted molecule's functional activity when compared to the NCN of the mRNA of one or more reporter genes of the reporter cells associated with other secreted molecules in a microwell or the NCN of the mRNA of one or more reporter genes of the reporter cells associated with an empty microwell.

Thus, the present invention provides an efficient method for analyzing a large number of secreting cells individually in a parallel manner rather than analyzing in a serial fashion a cell population and reporting the average measurement for the population. Each microwell, due to its small dimensions in the range of microns, facilitates rapid reaction rates, such as mRNA hybridization or capture of proteins. The proteins captured in the present invention are captured in a way to form an addressable array on a solid surface where the kinetic properties of the captured proteins can be analyzed en masse for binding affinity when reacted with labeled affinity ligands. The mRNA subsequently captured on an oligonucleotide capture support is from two sources: a) the secreting cell, for example, mRNA encoding the light and heavy chains of a monoclonal antibody secreted by a plasma cell, and b) one or more types of reporter cell(s). Although mRNA from an engineered reporter gene encoding a readily-assayable protein may be captured, reporter cells containing engineered reporter genes are not necessary in the present invention. This enables the use of un-engineered cell lines or even cells from a primary culture as reporter cells. The mRNA from one or more reporter genes (either engineered reporter genes or endogenous reporter genes) capable of responding to a receptor agonist, a receptor antagonist, or a modulator, is captured and the NCN of the mRNA can be quantified by NGS and effectively used in analyzing the therapeutic utility of the secreted molecules.

Thus, in some embodiments, the present invention provides a method of measuring the functional activity of a secreted molecule secreted by a secreting cell consisting of: placing one or more reporter cells into microwells; placing a plurality of secreting cells into the microwells such that a single secreting cell occupies a single microwell; allowing the secreting moieties to interact with the reporter cells; capturing and measuring selected mRNA from the reporter cells; and comparing the captured and measured selected mRNA to housekeeping mRNA within the reporter cells and thereby determining if the secreted moieties modulate the production of the selected mRNA within the reporter cells.

Other embodiments of the present invention provide a method of measuring a response of a reporter cell to a binding of a ligand to a receptor comprising the steps of: depositing into microwells a plurality of reporter cells, the reporter cells express a receptor on their surface; depositing into the microwells a plurality of secreting cells such that, on average, a single secreting cell occupies a single microwell; allowing the secreting cells to secrete a secreted molecule; optionally introducing into the microwells a ligand that interacts with the receptor; lysing the reporter cells; capturing mRNA of one or more reporter genes and optionally mRNA of one or more housekeeping genes from the reporter cells onto an oligonucleotide array placed in close proximity with the top of the microwells, the oligonucleotide array containing one or more unique DNA tags and an optional random code; converting mRNA from the reporter cells to cDNA, the mRNA coding for genes responding to the ligand-receptor binding and optionally for housekeeping genes not responding to ligand-protein binding; sequencing the cDNA and using the DNA tags and optional random codes to measure the response of the reporter cell to the binding of the ligand to the receptor.

In some aspects of these methods, the secreted molecule is an antibody. In some aspects, the receptor is a membrane bound protein permanently bound to the lipid bilayer, a peripheral membrane protein temporarily associated with lipid bilayer or an integral membrane protein, or a lipid-anchored protein bound to lipid bilayer bound through lipidated amino acid residues.

In some aspects, the volume of said microwells is between 10 and 1000 picoliters, and in some aspects, the number of reporter cells deposited into said microwells is between 1 and 500 cells per microwell. In some aspects, the number of nucleotides in said DNA tag is more than 6 nucleotides, and in some aspects, the number of nucleotides in said random code is more than 4 nucleotides. Further aspects of the embodiments provide DNA tags with unique optional random codes used to compute the ACN of the reporter gene and the ACN of the housekeeping gene, and in some aspects, the NCN of the ligand receptor binding is computed from the ration of the ACN of the reporter gene to the ACN of the housekeeping gene.

Other embodiments of the present invention provide a system or device for measuring a response of a reporter cell to a binding of a ligand to a receptor comprising the steps of: depositing into microwells a plurality of reporter cells, the reporter cells express a receptor on their surface; depositing into the microwells a plurality of secreting cells such that, on average, a single secreting cell occupies a single microwell; allowing the secreting cells to secrete a secreted molecule; optionally introducing into the microwells a ligand that interacts with the receptor; lysing the reporter cells; capturing mRNA of one or more reporter genes and optionally mRNA of one or more housekeeping genes from the reporter cells onto an oligonucleotide array placed in close proximity with the top of the microwells, the oligonucleotide array containing one or more unique DNA tags and an optional random code; converting mRNA from the reporter cells to cDNA, the mRNA coding for genes responding to the ligand-receptor binding and optionally for housekeeping genes not responding to ligand-protein binding; and sequencing the cDNA and using the DNA tags and optional random codes to measure the response of the reporter cell to the binding of the ligand to the receptor.

Yet another embodiment of the invention provides a method of measuring the functional activity of a secreted molecule secreted by a secreting cell consisting of: placing a plurality of secreting cells into microwells such that a single secreting cell occupies a single microwell and is secreting molecules; placing one or more reporter cells of one or more types into microwells; allowing copies of the secreted molecules to interact with a receptor of the reporter cells; capturing mRNA from one or more of the reporter genes of the reporter cells and capturing mRNA from one or more of the housekeeping genes of the reporter cells with an oligonucleotide capture support containing mRNA capture oligos on each feature comprising a unique DNA tag; converting captured mRNA into cDNA incorporating the DNA tag; sequencing the tagged and optionally coded cDNA by NGS; examining the sequenced cDNA from the one or more reporter genes and comparing it to the sequenced cDNA from the one or more housekeeping genes of the reporter cells to determine the functional activity of a secreted molecule secreted by a secreting cell.

Yet an additional embodiment of the invention provides a method of measuring a response of a reporter cell to a binding of a ligand to a receptor comprising the steps of: placing a plurality of ligands into microwells; placing one or more reporter cells of one or more types into the microwells; allowing a ligand to interact with a receptor of the reporter cells; capturing mRNA from one or more of reporter genes of the reporter cells with an oligonucleotide capture support containing mRNA capture oligos on each feature comprising a unique DNA tag; converting captured mRNA into cDNA incorporating the DNA tag; sequencing the tagged cDNA by NGS; examining the one or more sequenced cDNA from reporter genes to determine the response of a reporter cell to the binding of a ligand to a receptor.

Yet other embodiments of the present invention provide methods of determining whether two similar sequences are original molecules in a population of nucleic acid molecules or are duplicates created during sample preparation, e.g., PCR amplification, comprising: constructing a population of oligonucleotides containing a number of random codes, wherein the number of random codes is greater than the estimated number of molecules in the population of nucleic acid molecules; incorporating a single random code into every single molecule from a population of nucleic acid molecules; amplifying the population of nucleic acid molecules with the incorporated random codes; sequencing the amplified population of nucleic acid molecules with the incorporated random codes using a sequencing methodology that reports the sequence of individual nucleic acid molecules; and aggregating the reported sequences with the same random code into sequences representing original sequences in said population of nucleic acid molecules. In some aspects of this embodiment, the sequencing methodology is single molecule counting methodology, and in preferred aspects, the sequencing methodology is high throughput sequencing techniques known in the art.

These and other objects, advantages, and features of the invention will become apparent to those persons skilled in the art upon reading the details of the methods and embodiments of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1—Anatomy of two adjacent features and their mRNA capture probes on a DNA microarray FIG. 2—Detection of a receptor agonist.

FIG. 3—Detection of an inverse agonist, a type of receptor agonist.

FIG. 4—Detection of a modulator.

FIG. 5—Detection of a receptor antagonist.

DEFINITIONS

"Absolute Copy Number (ACN)"—The copy number of the responding or steady state levels of mRNA estimated by the count of independent cDNA molecules enumerated by NGS sequences derived from one or more cells based on random codes.

"Normalized Copy Number (NCN)"—the ratio of the Absolute Copy Number of the reporter gene mRNA to the Absolute Copy Number of a single housekeeping gene or any gene selected for use as a benchmark, or the average Absolute Copy Number of two or more housekeeping genes or any genes selected for use as a benchmark representing reporter cell housekeeping activity. The reporter cell housekeeping activity can be represented by the mRNA Absolute Copy Number of a single gene expressed by all reporter cells. Alternatively, the reporter cell housekeeping activity can be represented by the average mRNA Absolute Copy Number of two or more housekeeping genes. In the latter case, an average value must be computed from the Absolute Copy Numbers of the two or more housekeeping genes. The average value may be an arithmetic mean of the Absolute Copy Numbers, or it may be a weighted mean, the weights derived from the measured variation in Absolute Copy Numbers derived in previous runs, in the same run, or from published literature. Several weighting methods are known to those skilled in the art (Press, Numerical Recipes in C. The Art of Scientific Computing, 2nd Edition 1992).

As used herein, "molecules" or "biomolecules" are broad representations of moieties where not all of the interactions between atoms are covalently bonded. For example, two strands of DNA held together by various forces including Watson-Crick hydrogen bonding and base stacking balanced by the electrostatic repulsion of two phosphates either along the same strand or the opposite strands, are called a molecule as in cDNA molecules. Molecules can also be used to refer to protein complexes held together by various non-covalent bonding as in a complex formed by interacting ligand and its cognate receptor. Molecules and moieties are sometimes used interchangeably.

As used herein, "secreted molecules" are molecular entities secreted by a secreting cell as defined below.

As used herein, a "secreting cell" is a cell that releases one or more secreted molecules at rates that modify the local concentration of the secreted molecules inside a microwell.

As used herein, "nanofabrication" is the design and manufacture of devices with dimensions measured in nanometers or micrometers. An example of nanofabrication is the construction of microwells in a flexible material. In one specific embodiment, SU-8 photoresist (MicroChem Corporation, Newton, Mass.) is spin-coated onto a 10 cm silicon wafer in accordance with the manufacturer's recommendations. A pattern of 50 micron cubic micro-wells is exposed using ultraviolet light from a mask aligner (SUSS MicroTec AG, Schleissheimer Str. 90, 85748 Garching, Germany) in accordance with the manufacturer's recommendations and developed using SU-8 developer (MicroChem). Polydimethylsiloxane (PDMS) (SylGard Elastomer, Ellsworth Adhesives, Germantown, Wis.) is mixed, cured and removed in accordance with the manufacturer's recommendations.

As used herein, a "biologically active agent" is any agent that possesses activity in a biological system. Examples of biologically active agents include small molecule compounds; polypeptides, e.g., proteins; siRNAs; and oligonucleotides. A plurality of such biologically active agents would include, for example, 2 or more of such agents; in some cases, 3 or more agents; 5 or more agents; 10 or more agents; 20 or more agents; 50 or more agents; 100 or more agents; 500 or more agents; 1000 or more agents; 5000 or more agents; 10,000 or more agents; 30,000 or more agents; 100,000 or more agents; or 1,000,000 or more of such agents.

As used herein, the term "tag(s)" refers to a moiety that identifies the physical location of its origin. In one preferred embodiment, a tag is an oligonucleotide tag(s) associated with a physical location on an oligonucleotide capture support that correlates to the position of a microwell. The cDNA molecules having tags incorporated are herein referred to as "tagged cDNA" or "tagged cDNA molecules".

The term "oligonucleotide" as used herein includes linear oligomers of natural or modified monomers or linkages, including deoxyribonucleosides, ribonucleosides, anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3-4, to several tens of monomeric units, e.g. 40-60. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Usually oligonucleotides of the invention comprise the four natural nucleotides; however, they may also comprise non-natural nucleotide analogs. It is clear to those skilled in the art when oligonucleotides having natural or non-natural nucleotides may be employed, e.g. where processing by enzymes is called for, usually oligonucleotides consisting of natural nucleotides are required.

As used herein, a "selectable marker" is a gene introduced into a cell, especially a bacterium or to cells in culture that confers a trait suitable for artificial selection. Selectable markers may be a type of reporter gene used in laboratory microbiology, molecular biology, and genetic engineering to change the phenotype of a cell so as to indicate the success of a transfection or other procedure meant to introduce foreign DNA into a cell. Selectable markers may be antibiotic resistance genes, genes that cause an organism to fluoresce and the like.

As used herein, "transfection" is the process of deliberately introducing exogenous nucleic acids into eukaryotic cells; "transformation" is used to describe non-viral DNA transfer in bacteria, non-animal eukaryotic cells and plant cells; and "transduction" is used to describe virus-mediated DNA transfer.

As used herein, a "reporter gene" is a gene placed under the control of transcriptional regulatory elements and is engineered into a recombinant DNA construct and inserted into a cell or organism. Commonly used reporter genes that induce visually-identifiable characteristics usually involve fluorescent proteins or enzymes that act on a substrate to produce a luminescent product. Examples include the gene that encodes jellyfish GFP, the enzyme luciferase, and the red fluorescent protein from the gene dsRed. The GUS gene has been commonly used in plants. A common reporter in bacteria is the LacZ gene, which encodes the protein beta-galactosidase. An example of a selectable-marker which is also a reporter in bacteria is the chloramphenicol acetyltransferase (CAT) gene, which confers resistance to the antibiotic chloramphenicol. Though not a gene per se, as used herein, the term "reporter gene" also includes mRNA naturally transcribed by a cell; no visual or enzymatic modifications are needed. Furthermore, as used herein, reporter gene is any modified or unmodified endogenous gene of a cell.

As used herein, a "reporter cell" is an engineered cell into which a reporter gene has been inserted, or an un-engineered cell line, unmodified with an exogenously-added reporter gene, whose mRNA expression changes upon the interaction of one or more ligands with one or more molecules on the cell surface, or cells from primary culture.

As used herein, a "microelectromechanical systems device" or MEMS device means an apparatus with components or features with relatively small dimension between approximately 1 to 100 micrometers in size. The device enables miniaturization of biological assays such that single cell analysis is possible.

As used herein, "microwell" refers to sub millimeter structures with a volume between approximately 1 picoliter and 500 nanoliters. The microwell is typically constructed in a shape that allows dense packing on a planar substrate, i.e., the shape is triangular, rectangular, or hexagonal. Microwells can be either opened by removing one surface, usually at the top, or closed by placing the top in contact with other surfaces such as capture or support surfaces. The microwell can be homogeneous, or constructed out of dissimilar materials, including but not limited to glass, photoresist, or polydimethylsiloxane (PDMS).

As used herein, "kinetic properties" refer to the rates of reaction $k_{off}$, $k_{on}$, and their ratio $K_D$ between members of a protein complexes. For a binary protein complex, the dissociation constant $K_D$ is monotonically related to the Gibbs free energy which describes the work obtainable from an isothermal, isobaric process, conditions closely approximated in living systems.

As used herein, a "target binding protein" or "target protein" is a protein to which a biologically active agent of interest binds. The target binding protein could be a protein that typically binds to the biologically active agent of interest; for example, a cytokine, where the biologically active agent of interest is a receptor; or an antigen, where the biologically active agent of interest is an antibody. Alternatively, the target binding protein could be a protein that does not typically bind to the biologically active agent of interest; for example, a control cytokine.

As used herein, "binding agent" or "capture agent" is a molecule used to immobilize a biologically active agent. Capture agents can include but are not limited to oligonucleotides, DNA, RNA, protein, small molecules, peptides, aptamers, antibodies etc., which have an affinity for natural or artificial ligands.

As used herein, a "solid surface" or "solid support" is any sort of surface or support. It may be made of glass, plastics, nitrocellulose, polyvinylidene fluoride, or other highly non-reactive materials. A binding/capture agent may be attached (where the support may then be referred to as "a capture surface" or "capture support"), in which case the binding/capture agent may coat the solid surface, or may be distributed in discrete locations on the solid surface, for example in spots, localized into pads, or configured into a line. A DNA microarray is one of the many examples of a capture surface or capture support.

The term "monoclonal antibody" relates to an immunoglobulin made by a single clone of an antibody-producing cell. All monoclonal antibodies of the same specificity are identical except for natural mutants thereof. The term "antibody" as used herein is understood to mean intact molecules of immunoglobulins as well as fragments thereof (including but not limited to Fab, F(ab'), Fv, scFv).

As used herein, a "ligand" is a substance that is able to bind to and form a complex with a cognate receptor molecule.

The term "B cell" is used herein to mean an immune cell that is highly specialized for making immunoglobulins. A B cell is a lymphocyte and provides humoral immunity. A B cell produces an antibody that recognizes antigen molecules and can mature into a plasma cell. The term "plasma cell" is intended to mean a cell that develops from a B lymphocyte and can secrete immunoglobulins at high rate. Throughout this application the term "B cell" is intended to encompass "plasma cells" and vice versa. In general both are intended to encompass terms referring to cells which produce antibodies of interest.

Biologically active agents are characterized by their "binding affinity" to a given target biologically active agent, for example a protein. For example, an antibody is characterized by its affinity to a binding site or epitope.

As used herein, a "receptor agonist" is a molecular entity that binds to a receptor of a cell and triggers a response by that cell; an "inverse agonist" or "antagonist" is an agent that binds to the same receptor as an agonist but induces a response opposite to that of an agonist; and a "receptor antagonist" is a type of molecule that binds to a receptor but does not provoke a response but blocks or dampens other agonist-mediated responses. A "co-agonist" is any of a number of molecules that work together to form an agonist. Throughout this application the term "receptor agonist" is intended to also encompass "superagonist", "full agonist", "partial agonist", "partial inverse agonist", "full inverse agonist", "co-agonist", "allosteric agonist" or any other variants of agonist.

The term "receptor antagonist" is intended to encompass "competitive antagonist", "non-competitive antagonist", "uncompetitive antagonist", "silent antagonist" or any other variants of antagonist.

The term "modulator" is intended to encompass an agent modulating the activity of a naturally-occurring receptor agonist or receptor antagonist.

The term "random code" is used herein to mean a randomly generated DNA sequence of any length (i.e. 0 or more nucleotides) derived from an oligonucleotide with mixed bases (Ns) at strategic positions. These mixed bases can be consecutive or demarcated by specific bases (e.g. NNNGNNCNN). A random code of one or more nucleotides in combination with tag(s) enables counting of sequenced PCR amplified cDNA molecules generated from independent mRNA molecules to yield the Absolute Copy Number of mRNA of a reporter gene in a reporter cell. In circumstances where the random code is not needed it is included herein with a length of 0 nucleotides.

As used herein, the cDNA molecules having a random code incorporated are "coded cDNA" molecules.

As used herein, the term "Next Generation Sequencing" or NGS means a DNA sequencing technology that analyzes in a massively parallel manner single DNA molecule or a clonally amplified population of DNA molecules. Current examples of companies marketing such a technology are Roche 454, Ion Torrent from Life Technologies, and Illumina. Often millions of sequences are produced in a single run, compared to orders of magnitude fewer sequences produced by older technologies such as Sanger sequencing. The number of high quality nucleotides sequenced varies from 30 to 500 nucleotides. Each company's offering requires slightly different protocols to prepare samples and they consume different amounts of DNA.

As used herein, the term "a feature or features" means a microscopic DNA spot with a cluster of oligonucleotides attached to a defined location of the solid surface of a DNA microarray.

As used herein, "similar sequences" means nucleic acid sequences from the same molecule displaying the identical sequence or a sequence with nucleotide errors introduced by sample preparation or DNA sequencing methodology.

As used herein, "original molecule" means the molecule present in a sample population of nucleic acids prior to PCR amplification, not a molecule in that has been amplified from the sample population of nucleic acids.

As used herein, aggregating means to combine similar sequences with the same random code into a single sequence representing the nucleic acid sequence of the original molecule.

DETAILED DESCRIPTION OF THE INVENTION

This invention generally relates to methods, devices and kits for screening a plurality of secreting cells for functional activity by measuring the NCN of mRNA from one or more reporter genes produced by one or more types of reporter cells in response to secreted molecules acting as a receptor agonist, a receptor antagonist, or a modulator. In one embodiment, a plurality of secreting cells are placed in a plurality of microwells with a majority of microwells containing a single secreting cell. One or more types of reporter cells are also placed in the microwells. Secreted molecules by the secreting cells are captured on one or more support surfaces brought into contact with the microwells, at the same time, the secreted molecules are allowed to interact with the receptor on the reporter cells in the microwells as a receptor agonist or receptor antagonist. Subsequently the secreting cells and reporter cells are lysed releasing their mRNA. The mRNA encoding the secreted molecules, the mRNA from one or more reporter genes in one or more types of reporter cells, and housekeeping gene(s) from each type of reporter cells are captured on an oligonucleotide capture support containing mRNA capture oligos comprising a unique nucleotide tag and a random code at each feature on the oligonucleotide capture support corresponding to each microwell location. The captured mRNA on the oligonucleotide capture support is converted into cDNA incorporating the tags and optionally the random code, and tagged and coded cDNA is sequenced using NGS technology. The kinetic properties of the secreted molecules to one or more specific moieties are measured. The mRNA sequence encoding the secreted molecules is associated with the measured kinetic properties and Absolute Copy Number (ACN) of the mRNA of one or more reporter genes from each type of reporter cells is determined. The ACN of mRNA of housekeeping gene(s) of each type of reporter cells is determined and used to calculate the Normalized Copy Number (NCN) of mRNA of one or more reporter genes from each type of reporter cells. The NCN for a given secreted molecule is assessed and used in a manner analogous to the reporter cells currently sold and is well known to those skilled in the art.

Before the present invention is further described, it is to be understood that this invention is not limited to particular methods and devices described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell or sequence" may include a plurality of such cells or sequences and reference to "the well or addresses" may include reference to one or more wells or addresses and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The current invention is envisaged as one or more methods, one or more physical devices, and/or one or more kits, each covering the entirety or a portion of the invention. Screening means searching through a collection of many cells. The collection can contain many copies of the same cell, many copies of different cells, or both: many copies of many different cells.

Previous applications filed by the present inventors teach a method for measuring the kinetics of a molecule secreted from a secreting cell and determining the sequence of the mRNA coding for the secreted molecule. The present invention provides an improvement to these methods by teaching methods to perform tests for the functional activity of the secreted molecule. Functional activity generally refers to the modification of intracellular signaling due to the increase or decrease of binding of a ligand at a cellular receptor. Functional activity is distinct from antigen-antibody binding because, when eliciting an immune response from a host, an antigen must be a form convenient for host exposure as an immunogen. The form often may be distinct from the form active in a therapeutic situation. Furthermore, the host's focus upon introduction of foreign material is to identify and eliminate the pathogen, and one epitope is often as good as another. In a therapeutic situation, only specific epitopes may be useful for treating or modifying a disease or symptoms. Therefore, it is advantageous to test, for example, antibody-antigen interactions as close as possible to the situation presented in the therapeutic environment. Functional activity of, e.g., an antibody is much closer to a therapeutic situation, and a functional assay tests for functional activity. Such a functional assay is presented, e.g., in Example 1, where an un-engineered reporter cell line (HeLa) is used for identifying a TNF-α blocker, which can be useful in treating a variety of autoimmune diseases including psoriasis, employing the present invention.

U.S. Pat. No. 8,309,317 (Chen et al., Nov. 13, 2012), U.S. Pat. No. 8,309,035 (Chen et al., Nov. 13, 2012), and US Pub. No. 20110190148 (Chen et al., Aug. 4, 2011), each of which are incorporated herein for all purposes, describe a MEMS device that is used in the present invention. Briefly, microwells are fabricated into an elastomeric material on a MEMS device such that thousands of microwells fit in the area of a microscope slide. The microwells are open at the top. Secreting cells are dispersed from the top of the MEMS device and sink into the microwells after short period of time. The number of the secreting cells dispersed from the top of the MEMS device is less than the number of the wells so that, on average, a single cell occupies a single well.

Secreted molecules, such as antibodies produced in certain immune cells, e.g., plasma cells, are secreted at a high rate—often more than a thousand molecules per second. In microwells (having volumes of, e.g., 180 pL) such a rate results in a high concentration (approximately 1 nM) of secreted molecules in a short period of time (less than one minute). Sequential capture surfaces may be brought into contact with the secreting cells in the microwells in order to capture the secreted molecules from the secreting cells in the microwells. For example, a solid support coated with an antibody capture agent (e.g., Protein G, Protein A, etc.) may be used to contact the surface of the MEMS device to capture antibodies secreted by the plasma cell(s) contained in each microwell. Second, third, and so forth, similar antibody capture surfaces can be used sequentially to capture additional secreted antibodies, each capture resulting in an addressable antibody array reflecting the locations of all the plasma cells contained in the microwells. Each slide can be, for example, reacted with increasing concentrations of a fluorescently labeled antigen or a fluorescently labeled molecule related to the antigen in order to compute estimates of the dissociation constants and $k_{off}$. The specifics of kinetics measurements are further elaborated in U.S. Pat. No. 8,309,317 (Chen et al., Nov. 13, 2012), U.S. Pat. No. 8,309,035 (Chen et al., Nov. 13, 2012), and US Pub. No. 20110190148 (Chen et al., Aug. 4, 2011), which are incorporated herein in their entirety.

In addition, the secreting cells optionally may be lysed and their nucleic acid content (including mRNA) released. Messenger RNA encoding the secreted molecules from the secreting cells can be captured on an oligonucleotide capture support containing mRNA capture oligos comprising a unique nucleotide tag and a random code at each feature correlate to the position of a microwell. Captured mRNA on the oligonucleotide capture support is converted to cDNA incorporating the tags and optionally random code, and the tagged and coded cDNA is sequenced using NGS technology. Because the tags are unique to each location of the oligonucleotide capture support, the sequence of the tagged cDNAs can be related back to the microwell from which it was captured. Thus, the binding kinetics properties obtained from an antibody associated with a small area of the capture surface derived from a secreting cell contained in each microwell can be associated with the mRNA sequence of, e.g., both the light and heavy chains of an antibody. In addition, each cDNA sequence containing a distinct random code will be counted as an independent molecule. The count of the independent cDNA molecules is a good proxy of the responding or steady state levels of the mRNA at the time of cell lysis. As such, implementation of location-specific tags and molecule-specific random codes enables a parallel transcription analysis of the secreting cells and reporter cells by NGS to screen for functional activity of the secreted molecules (e.g., antibodies) as receptor agonists, receptor antagonists, or modulators. The specifics of mRNA sequencing and the association of sequencing with kinetics are further elaborated in U.S. Pat. No. 8,309,317 (Chen et al., Nov. 13, 2012), U.S. Pat. No. 8,309,035 (Chen et al., Nov. 13, 2012), and US Pub. No. 20110190148 (Chen et al., Aug. 4, 2011).

The present invention uses some of the processes described in U.S. Pat. No. 8,309,317 (Chen et al., Nov. 13, 2012), U.S. Pat. No. 8,309,035 (Chen et al., Nov. 13, 2012), and US Pub. No. 20110190148 (Chen et al., Aug. 4, 2011), in novel ways. In one embodiment, one or more reporter cells are deposited in the microwells of a MEMS device. The concentration of reporter cells is such that nearly every microwell is occupied by the reporter cells. By contrast, to maximize the chance of depositing a single secreting cell in a microwell, the concentration of the secreting cell is lower than that of the reporter cells; therefore there will be microwells unoccupied by the secreting cells. The reporter cells may be designed to produce readily assayable proteins in response to specific binding activity; alternatively, reporter cells that require no engineering may be used and changes in expression of endogenous genes in response to a specific binding activity may be adequate to report perturbation of the signal transduction event of a targeted pathway by a secreted molecule produced by a secreting cell.

An example of such an assay is screening of mouse plasma cells, a type of secreting cell secreting an antibody to an antigen (e.g., human TNF-α) that interacts with an endogenous receptor on one or more reporter cells; e.g., human embryonic kidney 293 cell line with an engineered reporter gene such as luciferase driven by a promoter regulated by a nuclear factor kappa B (NF-κB) response element to monitor the NF-κB signal transduction pathways, or HeLa (human epithelial carcinoma cell line) with the endogenous interleukin-6 gene as the reporter gene. Upon binding by human TNF-α to its cognate receptor on the surface of a reporter cell, endogenous NF-κB transcription factors are immobilized and bind to the DNA response elements inducing transcription of the downstream responding genes, including the reporter gene. The objective is to screen for a mouse antibody that will bind to human TNF-α and block TNF-α from interacting with its receptor to block activation of the NF-κB pathway. This is an example of screening mouse antibodies for a modulator.

In the present invention, the protein product (e.g., luciferase) is not measured; instead, the ACN of the responding mRNA levels of one or more reporter genes as well as optionally the ACN of the steady state mRNA levels from one or more housekeeping genes are measured by sequencing the tagged and optionally coded cDNA molecules corresponding to the mRNAs and counting the occurrence thereof. The present invention provides greater flexibility in the design of reporter cells, reduces the time required to measure the changes in the expression of a reporter gene, tremendously increases throughput by miniaturizing and parallelizing the assay, and eliminates the toxic (and often costly) chemicals used in reporter assays. With the ACNs of the mRNA levels of one or more reporter genes and ACNs of the mRNA of one or more housekeeping genes of the reporter cells measured, the NCN for the mRNA of a given reporter gene can be calculated. To ensure validity of the NCN, it is imperative that the secreting cells and reporter cells are of different origin (e.g., mouse plasma cells as secreting cells and engineered human HEK239 cell line or un-engineered HeLa cells (human) as reporter cells) such that the sequence of the housekeeping gene(s) used in determining the NCNs of the reporter gene in reporter cells is distinguishable from that of the housekeeping gene(s) of the secreting cells.

By comparing the NCN of reporter gene(s) of the reporter cells in those microwells unoccupied by secreting cells and the NCN of the reporter gene(s) from the reporter cells in those microwells containing secreting cells, one may assess the ability of a mouse plasma cell (e.g., a secreting cell) secreting an antibody to block the activity of human TNF-α. At the same time, the cDNA sequence of the variable domain for both the heavy and light chains of the antibody is determined. This variable domain sequence for both chains can then be used to generate a renewable source of the monoclonal antibody for further evaluation.

Anatomy of Two Exemplary and Adjacent Features with their mRNA Capture Probes on an Area of a DNA Microarray.

In this example, one feature will mate with a microwell containing one or more reporter cells. FIG. 1 shows a solid support 104 with two features, 103a and 103b, each consisting, for illustration purposes, of 5 oligonucleotides with the DNA sequence from the 5' end on the left and the 3' end on the right. In reality, there can be millions of oligonucleotides contained within each feature on a DNA microarray. At time point 107 the oligonucleotides are unoccupied and available to capture mRNA released from lysed cells. Along the length of each oligonucleotide, starting from the 5' end and moving toward the 3' end, there are 4 Ts serving as a spacer; tag regions 101a(b) represented by bases in bold type unique to each feature identifying the capture location; optional random code region 102a(b) represented by lower case letters unique to each oligonucleotide and allows the cDNA molecules to be accurately associated with the cognate independently-captured mRNA molecules. The random codes provide a numerical basis to correct any bias introduced by PCR amplification. Finally, there is mRNA capture region 100 which, in this example, can be one of two different sequences; one sequence can capture mRNA from a reporter gene and the other sequence can capture mRNA from a housekeeping gene.

At time point 108, the oligonucleotides on feature 103a(b) capture mRNA 105a1(b1) represented by heavy waved lines from the reporter gene and mRNA 105a2(b2) represented by thin waved lines from the housekeeping gene. These oligonucleotides serve to prime cDNA synthesis using the captured mRNA as a template. Those oligonucleotides capturing mRNA from the reporter gene yield cDNA 106a1(b1) represented by a thin broken line and those capturing mRNA from the housekeeping gene yield cDNA 106a2(b2) represented by a thick broken line. Once cDNA 106a1(b1) is amplified and sequenced by NGS technology, the mRNA capture location can be computed using the tag and the number of independent mRNAs captured—proportional to the levels of mRNA within the reporter cells and defined herein as the ACN of the reporter gene mRNA—can be inferred from the number of cDNA sequences bearing the same tag and a unique random code. The use of the random code enables correction of any bias in the cDNA molecule count introduced by PCR amplification. Similarly, cDNA 106a2(b2) can be counted to yield the ACN of the housekeeping gene mRNA of cells in the microwell mated to the second exemplary feature. Subsequently, the ratio of the ACN of the reporter gene mRNA and the ACN of the housekeeping gene mRNA defined herein as the NCN of the reporter gene mRNA from reporter cells in different microwells can be determined. The NCN as used herein assesses the activity of a secreted molecule by its effect on transcriptional changes of the reporter gene in reporter cells illustrated in various embodiments.

The following particular embodiments are examples of this invention and are not meant to exhaustively describe its application.

Embodiment 1—Detection of an Receptor Agonist

The methods of the present invention are used in certain embodiments to detect a secreted molecule that acts as a receptor agonist to a receptor on a reporter cell. Referring to FIG. 2, two adjacent microwells, 200a and 200b, viewed from the side of a MEMS device, are drawn at various time points 200, 201, 202, and 203. Multiple reporter cells 206 with cell surface receptors 214 are deposited in microwells 200a(b). Once reporter cells 206 have settled into each microwell, a single secreting cell 207a(b) is deposited into microwell 200a(b). Secreting cell 207a(b) secretes monoclonal antibody 208a(b) at time point 202. Monoclonal antibody 208a(b) diffuses throughout microwell 200a(b). Monoclonal antibody 208a binds to cell surface receptor 214 on reporter cell 206 and such a binding event is denoted as 209 at time point 202. Also at time point 202, monoclonal antibody 208b in microwell 200b does not bind to the cell surface receptors 214 and remains freely diffusing in microwell 200b. In between time points 202 and 203 a lysing agent is dispensed into microwells 200a(b) disrupting cells in the microwells and causing the release of the cells' mRNA content Immediately following lysis, at time point 203, an oligonucleotide capture support 204 containing 2 features consist of a population of capture oligonucleotides 205a(b) complementary to mRNA for, e.g., the heavy chain and light chain of the secreted antibody 208a(b) secreted by secreting cells 207a(b), the reporter gene(s) and the housekeeping gene(s) expressed in reporter cells 206 is brought into close proximity of microwells 200a(b) severely retarding diffusion of the mRNA out of the microwells. Alternatively, messenger RNA 210a(b) represented by super heavy waved lines for the heavy chain of the secreted molecule 208a(b), and mRNA 211a(b) represented by medium waved lines for the light chain of the secreted molecule 208a(b) from secreting cell 207a(b) diffuse and are captured by the appropriate capture oligonucleotides 205a(b). At the same time, the reporter gene mRNA 212a(b) represented by thin waved lines and the housekeeping gene mRNA 213a(b) represented by dotted lines from the reporter cells 206 in microwell 100a(b) diffuse and are captured by the appropriate capture probes 205a(b).

Oligonucleotide probes 205a(b) each contain a tag and an optional random code as detailed in FIG. 1. When cDNA molecules are synthesized from mRNA primed with the oligonucleotide probes 205a(b), every sequence with the same tag most likely will have incorporated a different random code. When tagged and coded cDNA is sequenced using NGS, those molecules with the same tags are collated and the random code is examined. As such, the random codes provide a direct way to count the original distribution of cDNA molecules reflecting the captured mRNA molecules and to calculate the ACN defined herein for the reporter gene mRNA 212a(b) despite any potential bias introduced, e.g., by PCR amplification of tagged and coded cDNA. The amount of captured mRNA molecules reflects the mRNA level of the responding reporter gene as well as that of the constitutive housekeeping gene. Similarly, the ACN for the housekeeping gene mRNA 213a(b) is determined.

In preferred embodiments, the ratio of the ACN for the reporter gene mRNA 212a(b) and ACN for the housekeeping gene mRNA 213a(b) is computed to yield the NCN of the reporter gene mRNA 212a(b) of the reporter cell 206 in a microwell whose location is delineated by the tag embedded in the cDNA molecules. The NCN for the reporter gene mRNA 212a of reporter cell 206 in microwell 200a—given the secreted molecule 208a acting as a receptor agonist—will increase compared to a) the NCN of the reporter gene mRNA 212b in microwell 200b containing the secreting cell 207b secreting a non-functional secreted molecule 208b that does not display a binding event similar to 209; or to b) the NCN of the reporter gene mRNA of the reporter cell in microwells containing no secreting cells.

Embodiment 2—Detection of an Inverse Agonist, a Type of Receptor Agonist

The methods of the present invention are used in certain embodiments to detect a secreted molecule that acts as a receptor agonist to a receptor on a reporter cell. Referring to FIG. 3, two adjacent microwells, 300a and 300b, viewed from the side of a MEMS device, are drawn at various time points 300, 301, 302, and 303. Multiple reporter cells 306 with cell surface receptors 314 are deposited in microwells 300a(b). Once reporter cells 306 have settled into each microwell, a single secreting cell 307a(b) is deposited into microwell 300a(b). Secreting cell 307a(b) secretes monoclonal antibody 308a(b) at time point 302. Monoclonal antibody 308a(b) diffuses throughout microwell 300a(b). Monoclonal antibody 308a binds to cell surface receptor 314 on reporter cell 306 and such a binding event is denoted as 309 at time point 302. Also at time point 302, monoclonal antibody 308b in microwell 300b does not bind to the cell surface receptors 314 and remain freely diffusing in microwell 300b. In between time points 302 and 303 a lysing agent is dispensed into microwells 300a(b) disrupting cells in the microwells and causing the release of the cells' mRNA content Immediately following lysis, at time point 303, an oligonucleotide capture support 304 containing 2 features consist of a population of capture oligonucleotides 305a(b) complementary to mRNA for the heavy chain and light chain of the secreted antibody 308a(b) secreted by secreting cells 307a(b), the reporter gene(s) and the housekeeping gene(s) expressed in reporter cells 306 is brought into close proximity of microwells 300a(b) severely retarding diffusion of the mRNA out of the microwells. Alternatively, messenger RNA 310a(b) represented by super heavy waved lines for the heavy chain of the secreted molecule 308a(b), and mRNA 311a(b) represented by medium waved lines for the light chain of the secreted molecule 308a(b) from secreting cell 307a(b) diffuse and are captured by the appropriate capture oligonucleotides 305a(b). At the same time, mRNA 312a(b) represented by thin waved lines for the reporter gene and mRNA 313a(b) represented by dotted lines for the housekeeping gene from the reporter cells 306 in microwell 300a(b) diffuse and are captured by the appropriate capture probes 305a(b).

Oligonucleotide probes 305a(b) each contain a tag and an optional random code as detailed in FIG. 1. When cDNA molecules are synthesized from mRNA primed with the oligonucleotide probes 305a(b), every sequence with the same tag most likely will have incorporated a different random code. When tagged and coded cDNA is sequenced using NGS, those molecules with the same tags are collated and the random code is examined. As such, the random codes provide a direct way to count the original distribution of cDNA molecules reflecting the captured mRNA molecules and to calculate the ACN defined herein for the reporter gene mRNA 312a(b) despite any potential bias introduced by PCR amplification of tagged and coded cDNA. The amount of captured mRNA molecules reflects the mRNA level of the responding reporter gene as well as that of the constitutive housekeeping gene. Similarly, the ACN for the housekeeping gene mRNA 313a(b) is determined.

In preferred embodiments, the ratio of the ACN for the reporter gene mRNA 312a(b) and ACN for the housekeeping gene mRNA 313a(b) is computed to yield the NCN of the reporter gene mRNA 312a(b) of the reporter cell 306 in a microwell whose location is delineated by the tag embedded in the cDNA molecules. The NCN for the reporter gene mRNA 312a of reporter cell 306 in microwell 300a—given the secreted molecule 308a acting as an inverse agonist—a type of receptor agonist, will decrease compared to a) the NCN of the reporter gene mRNA 312b in microwell 300b containing the secreting cell 307b secreting a non-functional secreted molecule 308b that does not display a binding event similar to 309; or to b) the NCN of the reporter gene mRNA of the reporter cell in microwells containing no secreting cells.

Embodiment 3—Detection of a Modulator

The methods of the present invention are used in certain embodiments to detect a secreted molecule that acts as a receptor agonist to a receptor on a reporter cell. Referring to FIG. 4, two adjacent microwells, 400a and 400b, viewed from the side of a MEMS device, are drawn at various time points 400, 401, 402, and 403. Multiple reporter cells 406 with cell surface receptors 414 are deposited in microwells 400a(b). Once reporter cells 406 have settled into each microwell, a single secreting cell 407a(b) is deposited into microwell 400a(b). Secreting cell 407a(b) secretes monoclonal antibody 408a(b) at time point 402. Monoclonal antibody 408a(b) diffuses throughout microwell 400a(b). At time point 402, a ligand 415 to the cognate receptor 414 on reporter cells 406 is introduced and is diffusing throughout microwell 400a(b). Monoclonal antibody 408a binds to the ligand 415 and such a binding event is denoted as 409 at time point 402. Also at time point 402, monoclonal antibody 408b in microwell 400b does not bind to the ligand 415 and remain freely diffusing in microwell 400b resulting in binding of the ligand 415 to the cognate receptor 414. In between time points 402 and 403 a lysing agent is dispensed into microwells 400a(b) disrupting cells in the microwells and causing the release of the cells' mRNA content. Immediately following lysis, at time point 403, an oligonucleotide capture support 404 containing 2 features consist of a population of capture oligonucleotides 405a(b) complementary to mRNA for the heavy chain and light chain of the secreted antibody 408a(b) secreted by secreting cells 407a(b), the reporter gene(s) and the housekeeping gene(s) expressed in reporter cells 406 is brought into close proximity of microwells 400a(b) severely retarding diffusion of the mRNA out of the microwells. Alternatively, messenger RNA 410a(b) represented by super heavy waved lines for the heavy chain of the secreted molecule 408a(b), and mRNA 411a(b) represented by medium waved lines for the light chain of the secreted molecule 408a(b) from secreting cell 407a(b) diffuse and are captured by the appropriate capture oligonucleotides 405a(b). At the same time, mRNA 412a(b) represented by thin waved lines for the reporter gene and mRNA 413a(b) represented by dotted lines for the housekeeping gene from the reporter cells 406 in microwell 400a(b) diffuse and are captured by the appropriate capture probes 405a(b).

Oligonucleotide probes 405a(b) each contain a tag and an optional random code as detailed in FIG. 1. When cDNA molecules are synthesized from mRNA primed with the oligonucleotide probes 405a(b), every sequence with the same tag most likely will have incorporated a different random code. When tagged and coded cDNA is sequenced using NGS, those molecules with the same tags are collated and the random code is examined. As such, the random codes provide a direct way to count the original distribution of cDNA molecules reflecting the captured mRNA molecules and to calculate the ACN defined herein for the reporter gene mRNA 412a(b) despite any potential bias introduced by PCR amplification of tagged and coded cDNA. The amount of captured mRNA molecules reflects the mRNA level of the responding reporter gene as well as that of the constitutive housekeeping gene. Similarly, the ACN for the housekeeping gene mRNA 413a(b) is determined.

In preferred embodiments, the ratio of the ACN for the reporter gene mRNA 412a(b) and ACN for the housekeeping gene mRNA 413a(b) is computed to yield the NCN of the reporter gene mRNA 412a(b) of the reporter cell 406 in a microwell whose location is delineated by the tag embedded in the cDNA molecules. The NCN for the reporter gene mRNA 412a of reporter cell 406 in microwell 400a—given the secreted molecule 408a acting as a modulator—will decrease compared to a) the NCN of the reporter gene mRNA 412b in microwell 400b containing the secreting cell 407b secreting a non-functional secreted molecule 408b that does not display a binding event similar to 409; or to b) the NCN of the reporter gene mRNA of the reporter cell in microwells containing no secreting cells.

Embodiment 4—Detection of a Receptor Antagonist

Yet another embodiment of the present invention is used to detect a secreted molecule that acts as a receptor antagonist to a receptor on a reporter cell. Referring to FIG. 5, two adjacent microwells, 500a and 500b, viewed from the side of a MEMS device, are drawn at various time points 500, 501, 502, and 503. Multiple reporter cells 506 with cell surface receptors 514 are deposited in microwells 500a(b). Once reporter cells 506 have settled into each microwell, a single secreting cell 507a(b) is deposited into microwell 500a(b). Secreting cell 507a(b) secretes monoclonal antibody 508a(b) at time point 502. Monoclonal antibody 508a(b) diffuses throughout microwell 500a(b). At time point 502, a ligand 515 to the receptor 514 on reporter cells 506 is introduced and is diffusing throughout microwell 500a(b). Monoclonal antibody 508a binds to the receptor 514 and such a binding event is denoted as 509 at time point 502. Also at time point 502, monoclonal antibody 508b in microwell 500b does not bind to the receptor 514 and remain freely diffusing in microwell 500b resulting in binding of the ligand 515 to the receptor 514. In between time points 502 and 503 a lysing agent is dispensed into microwells 500a(b) disrupting cells in the microwells and causing the release of the cells' mRNA content Immediately following lysis, at time point 503, an oligonucleotide capture support 504 containing 2 features consist of a population of capture oligonucleotides 505a(b) complementary to mRNA for the heavy chain and light chain of the secreted antibody 508a(b) secreted by secreting cells 507a(b), the reporter gene(s) and the housekeeping gene(s) expressed in reporter cells 506 is brought into close proximity of microwells 500a(b) severely retarding diffusion of the mRNA out of the microwells. Alternatively, messenger RNA 510a(b) represented by super heavy waved lines for the heavy chain of the secreted molecule 508a(b), and mRNA 511a(b) represented by medium waved lines for the light chain of the secreted molecule 508a(b) from secreting cell 507a(b) diffuse and are captured by the appropriate capture oligonucleotides 505a(b). At the same time, the reporter gene mRNA 512a(b) represented by thin waved lines and the housekeeping gene mRNA 513a(b) represented by dotted lines from the reporter cells 506 in microwell 500a(b) diffuse and are captured by the appropriate capture probes 505a(b).

Oligonucleotide probes 505a(b) each contain a tag and an optional random code as detailed in FIG. 1. When cDNA molecules are synthesized from mRNA primed with the oligonucleotide probes 505a(b), every sequence with the same tag most likely will have incorporated a different random code. When tagged and coded cDNA is sequenced using NGS, those molecules with the same tags are collated and the random code is examined. As such, the random codes provide a direct way to count the original distribution of cDNA molecules reflecting the captured mRNA molecules and to calculate the ACN defined herein for the reporter gene mRNA 512a(b) despite any potential bias introduced by PCR amplification of tagged and coded cDNA. The amount of captured mRNA molecules reflects the mRNA level of the responding reporter gene as well as that of the constitutive housekeeping gene. Similarly, the ACN for the housekeeping gene mRNA 513a(b) is determined.

In preferred embodiments, the ratio of the ACN for the reporter gene mRNA 512a(b) and ACN for the housekeeping gene mRNA 513a(b) is computed to yield the NCN of the reporter gene mRNA 512a(b) of the reporter cell 506 in a microwell whose location is delineated by the tag embedded in the cDNA molecules. The NCN for the reporter gene mRNA 512a of reporter cell 506 in microwell 500a—given the secreted molecule 508a acting as a receptor antagonist—will decrease compared to a) the NCN of the reporter gene mRNA 512b in microwell 500b containing the secreting cell 507b secreting a non-functional secreted molecule 508b that does not display a binding event similar to 509; or b) the NCN for the reporter gene mRNA 512a of reporter cell 506 in microwell 500a will roughly equal the NCN of the reporter gene mRNA of the reporter cell in microwells containing no secreting cells.

EXAMPLE

The following example is put forth so as to provide those of ordinary skill in the art with a complete disclosure and description of how to make and use the present invention, and is not intended to limit the scope of what the inventors regard as their invention nor is it intended to represent that the experiment below is all or the only experiment that could be performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Identification of a Murine Anti-Human TNF-α Antibody Functioning as a Modulator Immunization & Single Cell Suspension Generation.

Recombinant human TNF-α (rhTNF-α, Insight Genomics, Falls Church, Va.) is used to immunize young BALB/c mice with 50 µg rhTNF-α in Freund's complete adjuvant (Sigma-Aldrich, St. Louis, Mo.) by intraperitoneal injection (i.p.) on day 0. Fifty µg rhTNF-α in incomplete Freund's adjuvant (IFA, Sigma-Aldrich, St. Louis, Mo.) is then administered by subcutaneous injection (s.c.) on day 14 and on day 28, serum is collected on day 36 for titration, and 50 µg rhTNF-α in IFA is administered by s.c. on day 42, with a final boost with 100 µg rhTNF-α (intravenously only) on day 56. The spleen, along with serum, is harvested on day 59. A single cell suspension of the splenocytes is generated by disrupting the tissue via mashing between two frosted microscope slides using 10 mL of RPMI medium (ATCC, Manassas, Va.). The suspension is filtered through a 70 µm mesh (BD Biosciences, San Jose, Calif.) to remove clumps.

CD138+ Plasma Cell Isolation, Antibody Capture, and Antigen Interrogation.

Freshly isolated splenocytes from the above hyperimmunized mice are further processed using a commercial kit to enrich for plasma cells based on cell surface expression of CD138 (Miltenyi, Auburn, Calif.). Human cervical epithelial cells HeLa are used as the reporter cell and its endogenous Interleukin-6 gene as the reporter gene (ATCC, Manassas, Va.). HeLa cells are first spread at a concentration on a PDMS device such that deposition of 3 to 10 cells per microwells is favored. Afterwards, freshly enriched plasma cells are then spread on the same PDMS device at a lower cell concentration to favor deposition of a single cell per microwell. Antibody secreted from each plasma cell is captured on a derivatized microscope slide as described in U.S. Pat. No. 8,309,317 (Chen et al., Nov. 13, 2012), U.S. Pat. No. 8,309,035 (Chen et al., Nov. 13, 2012), and US Pub. No. 20110190148 (Chen et al., Aug. 4, 2011). Antigen-specific antibody secreting cells are identified by interrogating the antibody capture slide with increasing concentrations of fluorescently labeled rhTNF-α.

TNF Stimulation and mRNA Capture.

After antibody capture, the medium on the PDMS is exchanged with the same medium containing rhTNF-α at 20 ng/mL and cultured at 37° C. and 5% CO2 to allow stimulation of the reporter cell present in each microwell. For those microwells containing a plasma cell secreting an antibody that functions as a modulator, rhTNF-α will be bound by the antibody and not readily interact with the cognate receptor to activate the NF-kB signal transduction pathway in HeLa cells (reporter cells) present in the same microwell. After 30 minutes of incubation with rhTNF-α, the medium is removed and replaced with lysis buffer followed by prompt closure of the top of the microwells with a custom oligonucleotide capture support (NimbleGen, Madison, Wis.), as described in U.S. Pat. No. 8,309,317 (Chen et al., Nov. 13, 2012), U.S. Pat. No. 8,309,035 (Chen et al., Nov. 13, 2012), and US Pub. No. 20110190148 (Chen et al., Aug. 4, 2011). The custom oligonucleotide capture support is prepared such that each feature contains capture probes for mRNAs for all subclasses (1, 2a, 2b, and 3) of the murine IgG heavy chain gene, the murine Ig kappa light chain gene, and the murine Ig lambda light chain gene. Additionally, the oligonucleotide capture probes are expanded for the present invention to include the human Interleukin-6 (IL-6) gene (reporter gene), and the human glyceraldehyde-3-phosphate dehydrogenase (GAPDH) gene (housekeeping gene). Hybridization is allowed to proceed overnight. In addition, each oligonucleotide capture probe contains a unique tag specifying the coordinate in relation to each microwell and an optional random code for facilitating counting of independent cDNA fragments sequenced with NGS to measure the independently captured mRNA molecules, which reflect the responding level of reporter gene mRNA and the constitutive level of housekeeping gene mRNA.

cDNA Synthesis, PCR Amplification, and NGS.

Captured mRNA on the oligonucleotide capture support are converted into cDNA. A unique tag and an optional random code is incorporated into each cDNA to allow for matching of mRNA to microwells and measurement of the independently captured mRNA. The tagged and coded cDNA fragments of the following mRNA molecules are then amplified: variable domain of IgG heavy chain subclasses, variable domain of Ig kappa light chain, variable domain of lambda light chain, a fragment of the human Inteukin-6 gene, and a fragment of the human GAPDH gene. The amplicons are then sequenced by NGS on a MiSeq (Illumina, San Diego, Calif.) with the 2×250 bp chemistry.

Bioinformatic Analysis of Images and DNA Sequences.

All fluorescent images are scanned at 532 nm on an Axon 4000A (10 micron resolution) and the files are processed using Mathematica 8.0 (Wolfram Research). Three images of every slide are scanned at various photomultiplier voltages. Image files are processed in proprietary Mathematica algorithms in order to identify a) small areas with shapes of the microwells; b) signal intensities that are statistically significant; and c) consistent baseline values.

Intensity values for each of 3 reaction concentrations (10 pM, 100 pM, 1 nM) and 3 additional time points after wash are recorded. Concentration values are used to estimate the $K_D$ and signal amplitude that minimize the squared sum of the difference between the expected and measured signals, commonly termed the Chisquared, $$\chi^2 = \sum_{i=1}^{3}\left(\text{Signal}_i - \frac{\text{Amp } Conc_i}{Conc_i + K_D}\right)^2 \qquad \text{Equation 1}$$

Bioinformatic Analysis of Images and DNA Sequences.

$\text{Signal}_i$ is the measured digital value (0-65535), $Conc_i$ is one of {10 pM, 100 pM, 1 nM}, and Amp and $K_D$ are parameters varied until a minimum is reached. $k_{off}$ is estimated from the 1 nM signal plus the three ensuing washes by minimizing a similar difference between the expected and measured signals:

$$\chi^2 = \sum_{i=1}^{4}(\text{Signal}_i - \text{Amp}\, e^{-k\, Time_2})^2 \qquad \text{Equation 2}$$

$\text{Signal}_i$ is the measured digital value (0-65535), $Time_i$ is one of {5 min, 15 min, 45 min or 105 min}, and Amp and k are parameters varied until a minimum is reached. k is commonly called $k_{off}$, measured in sec−1, and is the reciprocal of the time needed for 63% of the bound antigen to dislodge from their respective antibodies. $k_{on}$ is computed as $k_{off}/K_D$. Antibody $k_{on}$ and $k_{off}$ values are summarized and displayed in a logarithmic plot.

Illumina generated sequences are analyzed using a battery of proprietary algorithms developed with Mathematica 8. A modified Hamming code is used to construct tags that correct for single base errors. A tag is identified in each DNA sequence and matched to the physical locations on the NimbleGen chip. The NimbleGen locations are subsequently matched to scanning coordinates on the antibody capture slide.

The DNA sequences of the paired heavy and light chain of the murine IgG variable domains mapped to those coordinates on the antibody capture slide identified by fluorescently labeled rhTNF-α will allow reconstruction of an antibody that binds to TNF-α. These identified murine IgG variable domains are referred to as TNF-α binder candidates. The DNA sequences containing the human IL-6 gene with the tag identical to that of a TNF-α binder candidate are collated; the random code in each of these human IL-6 gene-containing sequences is compared among each other to assess the number of independent cDNA molecules to determine the ACN of the human IL-6 gene mRNA associated with a microwell that identified one of the TNF-α binder candidate. Similarly, the DNA sequences containing the human GAPDH gene with the tag identical to that of the TNF-α binder candidates are also collated; the random code in each of these human GAPDH-containing sequences is compared among each other to assess the number of independent cDNA molecules to determine the ACN of the human GAPDH gene mRNA. Having available the ACN of human IL-6 gene mRNA and the ACN of human GAPDH gene mRNA for associated with a TNF-α binder candidate, the NCN of the human IL-6 gene mRNA associated with a TNF-α binder candidate can be computed and the activity of such a TNF-α binder candidate functions as a modulator can be assessed.

The preceding merely illustrates the principles of the invention. It should be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A method of measuring the functional activity of a secreted molecule secreted by a secreting cell consisting of:
placing a plurality of secreting cells into microwells such that a single secreting cell occupies a single microwell and is secreting molecules;
placing one to five hundred reporter cells of one or more types into each microwell occupied by a single secreting cell;
allowing a concentration of secreted molecules in each microwell to reach 1 nM or more;
allowing the secreted molecules to interact with a receptor of the reporter cells in the microwells;
lysing the secreting cells and reporter cells;
capturing mRNA from the secreting cells and mRNA from one or more engineered reporter genes of the reporter cells and mRNA from one or more housekeeping genes of the reporter cells from the microwells with an oligonucleotide capture support containing mRNA capture oligos where the mRNA capture oligos comprise converting captured mRNA into cDNA incorporating the DNA tag and random code;

converting captured mRNA into cDNA incorporating the DNA tag;

sequencing the tagged cDNA by next generation sequencing (NGS);

examining the sequenced cDNA from the one or more engineered reporter genes of the reporter cells;

using the DNA tags and random codes to compute an Absolute Copy Number (ACN) of the engineered reporter genes and an ACN of the housekeeping genes for the reporter cells in each well;

using a ratio of the ACN of the engineered reporter genes to the ACN of the housekeeping genes to compute a Normalized Copy Number (NCN) of the engineered reporter genes for the reporter cells in each well;

examining the mRNA sequences encoding the secreted molecules from the secreting cells in each well; and for each well, associating the mRNA sequences encoding the secreted molecules from the secreting cells with the NCN of the mRNA from the engineered reporter genes.

2. The method of claim 1 wherein the secreted molecule is an antibody.

3. The method of claim 1 wherein the reporter cells originate from an organism distinct from that of the secreting cell.

4. The method of claim 1 wherein the number of nucleotides in the random code is more than 4 nucleotides.

5. The method of claim 1 wherein the receptor is a membrane bound protein permanently bound to a lipid bilayer of the reporter cell, a peripheral membrane protein temporarily associated with the lipid bilayer or integral membrane protein, or a lipid-anchored protein bound to the lipid bilayer through lipidated amino acid residues.

6. The method of claim 1 wherein the volume of the microwells is between 10 and 1000 picoliters.

7. The method of claim 1 wherein the number of nucleotides in the DNA tag is more than 6 nucleotides.

* * * * *